US006054490A

United States Patent [19]
Sime et al.

[11] Patent Number: 6,054,490
[45] Date of Patent: Apr. 25, 2000

[54] USE OF SESQUITERPENES FOR INHIBITING OXIDATIVE ENZYMES

[75] Inventors: John Thomas Sime; Peter Samuel James Cheetham; Michelle Lorraine Gradley, all of Kent; Nigel Eric Banister, London, all of United Kingdom

[73] Assignee: Zylepsis Limited, United Kingdom

[21] Appl. No.: 08/952,131

[22] PCT Filed: May 9, 1996

[86] PCT No.: PCT/GB96/01118

§ 371 Date: Apr. 10, 1998

§ 102(e) Date: Apr. 10, 1998

[87] PCT Pub. No.: WO96/35415

PCT Pub. Date: Nov. 14, 1996

[30] Foreign Application Priority Data

May 9, 1995 [GB] United Kingdom .................... 9509321

[51] Int. Cl.$^7$ ..................................................... A61K 31/00
[52] U.S. Cl. .......................... 514/675; 514/724; 514/762; 514/763; 514/766; 568/303
[58] Field of Search ..................................... 514/675, 724, 514/762, 763, 766; 568/303

[56] References Cited

U.S. PATENT DOCUMENTS 5,057,501  10/1991  Thornfeldt ................................. 514/53

FOREIGN PATENT DOCUMENTS

| 58-162541 | 9/1983 | Japan . |
| 61-129140 | 6/1986 | Japan . |
| 61-129140 | 7/1986 | Japan . |
| 04 346 925 | 12/1992 | Japan . |
| 06303967 | 11/1994 | Japan . |
| 2256271 | 10/1993 | United Kingdom . |

OTHER PUBLICATIONS

Soons et al. (1991) "Pharmacokinetics and Drug Disposition, Grapefruit juice and cimetidine inhibit stereoselective metabolism of nitrendipine in humans," Clin. Pharmacol. Ther. 50:394–403.

Edgar et al. (1992) "Acute effects of drinking grapefruit juice on the pharmacokinetics and dynamics on felodipine—and its potential clinical relevance," Eur. J. Clin. Pharmacol. 42:313–317.

Merkel et al. (1994) "Grapefruit juice inhibits 7–hydroxylation of coumarin in healthy volunteers," Eur. J. Clin. Pharmacol. 46:175–177.

Bailey et al. (1994) "Grapefruit juice and drugs. How significant is this reaction?" Clin Pharmacokin. 26(2):91–98.

Yee et al. (1995) "Effect of grapefruit juice on blood cyclosporin concentration," Lancet 345:955–957.

Ducharme et al. (1993) "Trough concentrations of cyclosporine in blood following administration with grapefruit juice," Brit. J. Clin. Pharmacol. 36:457–459.

Willershausen et al. (1991) "Enzymatische transformation von Valencen zu Nootkaton," Chemiker–Zeitung 115(12):358–360.

Pfau et Plattner (1939) "Etudes sur les matières végétales volatiles X$^1$. Sur les vétivones, constituants, odorants des essences de vétvier," Helv. Chim. Acta. 22:640–654.

Wani et al. (1971) "Plant Antitumor Agents. VI. The Isolation and Structure of Taxol, a Novel Antileukemic and Antitumor Agent from *Taxus brevifolia*," J. Am. Chem. Soc. 93:2325–2327.

Kingston et al. "Synthesis and Structure–Activity Relationships of Taxol Derivatives as Anticancer Agents," in *Studies in Organic Chemistry*, vol. 26 entitled "New trends in natural products chemistry," Atta–ur–Rahman, P.W. Le Quesne, Eds., Elsvier, Amsterdam, 1986, pp. 219–235.

Guengerich et al. (1991) "Expression of Mammalian Cytochrome P450 Enzymes Using Yeast–Based Vectors," Methods Enzymol. 206:130–145.

Omura and Sato (1964) "The Carbon Monoxide–binding Pigment of Liver Microsomes," J. Biol. Chem. 239:2370–2378.

Jefcoate (1979) "Measurement of Substrate and Inhibitor Binding to Microsomal Cytochrome P–450 by Optical–Difference Spectroscopy," Methods Enzymol. 52:258–296.

Lowry et al. (1951) "Protein Measurement with the Folin Phenol Reagent," J. Biol. Chem. 31:265–275.

Mehmood et al. (1995) "Metabolism of the Herbicide Chlortoluron by Human Cytochrome P450 3A4," Chemosphere 31:4515–4529.

Dror et al. (1995) "Stabilization of microbial cytochrome P–450 activity by creation of stationary–phase conditions in a continuously operated immobilized cell reactor," Appl. and Environ. Micro. 61(3):855–859.

Belisario et al. (1991) "Effect of avarol, avarone and nine of their natural and synthetic derivatives on microsomal drug––metabolizing enzymes," Toxicol. Lett. 57(2):183–193.

Chapman et al. (1991) "In vivo and in vitro effects of helenalin on mouse hepatic microsomal cytochrome P450," Biochem. Pharmacol. 41(2):229–235.

Chapman et al. (1989) "In vitro inhibition of mouse hepatic mixed–function oxidase enzymes by helenalin and alantolactone," 38(22):3913–3923.

Kim et al. (1987) "Subchronic Treatment with Gossypol and Liver Microsomal Drug Metabolizing Enzyme System of Male Hamsters," Adv. Contracept. Delivery Sys. 3:183–194.

Samuelson (1992) "Sesquiterpenoids and Diterpenoids with Pharmacological and Biological Activities," Acta Pharm. Fenn. 101(2):33–34.

(List continued on next page.)

*Primary Examiner*—Dwayne C. Jones
*Assistant Examiner*—C. Delacroix-Muirheid
*Attorney, Agent, or Firm*—Medlen & Carroll, LLP

[57] ABSTRACT

The invention relates to the use of a sesquiterpene for inhibiting an oxidative enzyme, preferably a cytochrome P450 enzyme. The invention also relates to compositions comprising a sesquiterpene and a drug which exhibits instability in the presence of an oxidative enzyme.

36 Claims, 1 Drawing Sheet

OTHER PUBLICATIONS

Yamahara et al. (1990) "Anti–Ulcer Effects in Rats of Bitter Cardamon Constituents," Chem. Pharm. Bull 38(11):3053–3054.

Chapman et al., Biochemical Pharmacology. 38(22), (1989), 3913–23.

Belisario et al., *Toxicology Letters* 57, 183–193, 1991.

Japio AN 86–129140, Kinoshita et al., JP 61121940 A (abstract), 1986.

Figure 1

USE OF SESQUITERPENES FOR INHIBITING OXIDATIVE ENZYMES

FIELD OF THE INVENTION

This application is a 371 of PCT/GB96/01118 filed May 4, 1996.

The present invention relates to substances and methods for inhibiting oxidative enzymes, and in particular for inhibiting enzymes responsible for the metabolism of bioactive agents to inactive or excretable derivatives thereof in vivo.

BACKGROUND OF THE INVENTION

Metabolism of bioactive agents (hereafter "drugs") to inactive or excretable derivatives is undesirable in many treatment regimes because it leads to a reduction in bioavailability. This may necessitate increasing dosage of the drug and this can lead to adverse side effects. The most significant enzymes responsible for such metabolism are the cytochrome P450 enzymes such as the CYP3A4 isozyme. Most agents known to inhibit CYP3A4 have significant adverse effects that make them unsuitable for co-administration with the drug.

The present invention aims to overcome these and other problems of the prior art.

SUMMARY OF THE INVENTION

The present invention relates to compositions comprising a pharmaceutically acceptable carrier, a compound which is unstable in the presence of an oxidative enzyme, and a sesquiterpene. In preferred embodiments, the present invention relates to compositions comprising: i) a pharmaceutically acceptable carrier; ii) a compound which is unstable in the presence of an oxidative enzyme; and iii) a sesquiterpene selected from the group consisting of nootkatol, nootkatone, nootkatol isomers, nootkatone isomers. In particular embodiments, the compound which is unstable in the presence of an oxidative enzyme is selected from the group consisting of taxol, cyclosporin, and dihydropyridine.

In other preferred embodiments, the present invention relates to compositions comprising: i) a pharmaceutically acceptable carrier; ii) a compound that is unstable in the presence of an oxidative enzyme, which is selected from the group consisting of taxol, cyclosporin, and dihydropyridine; and iii) a sesquiterpene. In particular embodiments, the sesquiterpene is selected from the group consisting of nootkatol, nootkatone, nootkatol isomers, nootkatone isomers, bicyclic sesquiterpenes, substituted sesquiterpenes, and oxidized sesquiterpenes.

In one embodiment of the inventive compositions, the sesquiterpene comprises approximately 0.1 to 10% of the invention composition. In certain embodiments, the inventive composition is in the form of a solid or a liquid, and is suitable for oral or intravenous administration to humans. In yet other embodiments, the invention composition comprises a compound which is unstable in the presence of cytochrome P450 oxidative enzyme. In particular embodiments, the cytochrome P450 enzyme is cytochrome P450 3A4.

Furthermore, the present invention relates to methods for inhibiting the action of at least one oxidative enzyme. In preferred embodiments, the present invention relates to methods for inhibiting the action of at least one oxidative enzyme, comprising the steps of: a) providing in any order: i) a composition comprising a pharmaceutically acceptable carrier, a compound which is unstable in the presence of an oxidative enzyme, and a sesquiterpene selected from the group consisting of nootkatol, nootkatone, nootkatol isomers and nootkatone isomers, and ii) one or more oxidative enzymes; and b) exposing the composition to one or more oxidative enzymes under conditions such that one or more oxidative enzymes is inhibited. In particular embodiments, the compound which is unstable in the presence of an oxidative enzyme is selected from the group consisting of taxol, cyclosporin, and dihydropyridine.

In other preferred embodiments, the present invention relates to methods for inhibiting the action of at least one oxidative enzyme, comprising the steps of: a) providing in any order: i) a composition comprising a pharmaceutically acceptable carrier, a sesquiterpene, and a compound that is unstable in the presence of an oxidative enzyme, which is selected from the group consisting of taxol and cyclosporin, and ii) one or more oxidative enzymes; and b) exposing the composition to said one or more oxidative enzymes under conditions such that one or more oxidative enzymes is inhibited. In particular embodiments, the sesquiterpene is selected from the group consisting of nootkatol, nootkatone, nootkatol isomers, nootkatone isomers, bicyclic sesquiterpenes, substituted sesquiterpenes, and oxidized sesquiterpenes.

In one embodiment, the inventive method provides a sesquiterpene comprising approximately 0.1 to 10% of the composition provided. In certain embodiments, the inventive method provides a composition in the form of a solid or a liquid, and is suitable for oral or intravenous administration to humans. In other embodiments, the inventive method provides a compound which is unstable in the presence of cytochrome P450 oxidative enzyme. In particular embodiments, the cytochrome P450 enzyme is cytochrome P450 3A4. In yet other embodiments, the inventive method inhibits one or more oxidative enzymes in vitro.

Further, the present invention relates to methods for preparing a pharmaceutical composition. In preferred embodiments, the present invention relates to methods for preparing a pharmaceutical composition comprising the steps of: a) providing in any order: i) a sesquiterpene selected from the group consisting of nootkatol, nootkatone, nootkatol isomers, and nootkatone isomers, ii) a pharmaceutically acceptable carrier, and iii) a compound which is unstable in the presence of an oxidative enzyme; and b) combining the sesquiterpene, the pharmaceutically acceptable carrier, and the compound which is unstable in the presence of an oxidative enzyme under conditions such that a pharmaceutical composition is produced. In particular embodiments, the compound which is unstable in the presence of an oxidative enzyme is selected from the group consisting of taxol, cyclosporin, and dihydropyridine.

In other preferred embodiments, the present invention related to methods for preparing a pharmaceutical composition comprising the steps of: a) providing in any order: i) a sesquiterpene, ii) a pharmaceutically acceptable carrier, and iii) a compound that is unstable in the presence of an oxidative enzyme, which is selected from the group consisting of taxol and cyclosporin; and b) combining the sesquiterpene, the pharmaceutically acceptable carrier, and the compound which is unstable in the presence of an oxidative enzyme under conditions such that a pharmaceutical composition is produced. In particular embodiments, the sesquiterpene is selected from the group consisting of nootkatol, nootkatone, nootkatol isomers, nootkatone isomers, bicyclic sesquiterpenes, substituted sesquiterpenes, and oxidized sesquiterpenes.

In one embodiment, the inventive method produces a sesquiterpene comprising approximately 0.1 to 10% of the composition provided. In certain embodiments, the inventive method provides a composition in the form of a solid or a liquid. In other embodiments, the inventive method further comprises the step of administering the pharmaceutical composition to a human, wherein the administration is selected from the group consisting of oral administration and intravenous administration. In other embodiments, the inventive method provides a compound which is unstable in the presence of cytochrome P450 oxidative enzyme. In particular embodiments, the cytochrome P450 enzyme is cytochrome P450 3A4. In one embodiment, the inventive method provides a pharmaceutical composition that is stable in vivo. In other embodiments, the inventive method provides a pharmaceutical composition that is stable in vitro.

The present invention also relates to methods for selecting a sesquiterpene with inhibitory activity on an oxidative enzyme for use in pharmaceutical compositions, comprising the steps of: a) providing a test sesquiterpene, a substrate, and one or more oxidative enzymes; b) exposing the test sesquiterpene and substrate to one or more oxidative enzymes to form a test complex; c) monitoring the test complex for inhibition of the oxidative activity of the oxidative enzyme(s); d) selecting the test sesquiterpene showing an inhibitory activity on the oxidative enzyme(s) to provide an inhibitory sesquiterpene; and e) using the inhibitory sesquiterpene to produce a pharmaceutical composition. In one embodiment, monitoring of the test complex is accomplished by measuring the hydroxylation of the substrate by one or more oxidative enzymes. In particular embodiments, the substrate is steroid 4-androstene-3,17-dione. In other particular embodiments, the oxidative enzyme is *Bacillus megaterium* oxidative enzyme. In preferred embodiments, the test sesquiterpene is selected from the group consisting of nootkatol, nootkatone, nootkatol isomers, and nootkatone isomers, bicyclic sesquiterpenes, substituted sesquiterpenes, and oxidized sesquiterpenes. In other embodiments, the pharmaceutical composition further comprises a pharmaceutically acceptable carrier and a compound which is unstable in the presence of an oxidative enzyme.

DESCRIPTION OF THE INVENTION

The effect of grapefruit juice on the bioavailability of some drugs has been reported recently. [Soons et al, *Clin. Pharmacol. Ther.,* 1991, 50, 394; Edgar et al, *Eur. J. Clin. Pharmacol.,* (1992) 42, 313–317; and *J. Clin. Pharmacol.,* 1994, 46, 175—for the hydroxylation of coumarin (CAS No 91-64-5)]. For example, Bailey et al, (1994) *Clin. Pharmacokinet.,* 26(2), 91–98 showed that concomitant administration of a glass of regular strength grapefruit juice (200 ml) more than doubled the mean maximal plasma concentration ($C_{max}$) and area under the curve plasma concentration —time curve (AUC) of Felodipine, a dihydropyridine calcium antagonist for the standard (non-controlled release) tablet compared with $C_{max}$ and AUC values after administration of the drug with water. Because first-pass (pre-systemic) metabolism in the small intestinal wall and liver is the reason for an average bioavailability of felodipine of 15% after oral administration with water, it is likely that grapefruit juice inhibits first-pass metabolism. Similar effects were shown for other dihydropyridine calcium antagonists.

It has been asserted that the ingredient in grapefruit juice responsible for the above inhibitory effect is a bioflavonoid (Yee et al., *The Lancet,* 1995, 345, 955; *Br. J. Clin. Pharmac.,* 1993, 36, 457) and probably naringin which is present at a concentration of approximately 90 mg/200 ml of grapefruit juice. However, compared with grapefruit juice, naringin solution produced less interaction with felodipine in all volunteers tested by Bailey et al (1994).

The sesquiterpene compound, nootkatone, is one of the primary contributors to the distinctive flavour and aroma of grapefruit. Nootkatone expression in the fruit is linked to the maturity of the fruit and is associated with the maturation process.

In addition to plant produced nootkatone a number of enzyme systems produced by organisms other than higher plants have the capability of converting synthetic precursors of nootkatone to nootkatone itself. Thus, for example, a variety of microorganisms can oxidise valencene to nootkatone.

Whilst investigating such transformations as effected by bacteria and fungi, it was deduced that the conversion was the result of two oxidative steps. The first was indicated to be carried out by an enzyme thought to be a cytochrome P450 or related enzyme system. The second appeared as an oxidoreductase transformation.

During elucidation of these enzymic steps it was, unexpectedly, discovered that nootkatone acts as an inhibitor of the first enzyme catalysed oxidative step. This surprising effect was observed in many organisms, both eukaryotes and prokaryotes. Nootkatone was demonstrated to have use as an inhibitor of these enzyme systems in vivo.

The inventors have shown that their discovery of this inhibitory property of sesquiterpenes, particularly oxidised sesquiterpenes such as nootkatol and nootkatone or isomers of nootkatone eg. α-vetivone can be extended to enzymes responsible for drug metabolism in vivo in mammalian systems. In particular, the effect of cytochrome P450 enzymes and related enzyme systems which process drugs and xenobiotics in mammals can be modified.

According to the invention there is provided a sesquiterpene for use as a medicament.

In a second aspect of the invention provides a sesquiterpene for use in the inhibition of an oxidative enzyme.

The inhibition of an oxidative enzyme can be readily determined by a skilled person in an in vitro test in which the consumption of oxygen by the oxidative enzyme is measured in the presence or absence of a sesquiterpene of the invention. The total inhibition or reduction of oxygen consumption in the presence of a sesquiterpene is indicative of an inhibitory effect of the invention.

In a third aspect the invention provides the use of a sesquiterpene in the manufacture of a composition for stabilising a drug compound in vivo, or in vitro, wherein the drug compound exhibits instability in the presence of one or more oxidative enzymes.

In a fourth aspect the invention provides a selection method comprising screening a test sesquiterpene compound for an inhibitory effect on the oxidative activity of an enzyme and, if the test compound displays an inhibitory effect, using the compound in the manufacture of a medicament.

By "inhibitory" we include the meaning that the sesquiterpene reduces the extent of metabolism of the drug in vitro at a concentration of 500 $\mu$g/ml and preferably 100 $\mu$g/ml or less.

Preferably, the inhibitory effect is screened by measuring the hydroxylation of the steroid 4-androstene-3,17-dione by the oxidative enzyme system of *Bacillus megaterium* (ATCC 13368).

Alternatively, the inhibitory effect can be screened by measuring the hydroxylation of valencene to nootkatol, using the methods described in Japanese patent 06303-967/1991 or Chemiker-Zeitung, 1991, 115, 358; the disclosures of which are incorporated herein by reference.

The terpenes are a class of natural products having a structural relationship to isoprene (1a)

Terpenes are classified according to the number of isoprene units of which they are composed.

Sesquiterpenes are $C_{15}$ hydrocarbons or their oxygenated analogs. They arise from the cyclization of farnesylpyrophosphate and subsequent rearrangements of the resulting carbonium ions (XIV and XV), as in reaction (3), where OPP represents oxygen-alkylated pyrophosphate. Almost all known sesquiterpenes can be derived from these two cations.

Many sesquiterpenes are important constituents of the characteristic aromas of plant products.

The preferred sesquiterpenes of the present invention are preferably substituted and advantageously bicyclic. The most preferred bicyclic sesquiterpenes are oxidised. Advantageously, the oxidised sesquiterpenes are the products of oxidation of valencene, nootkatol and more preferably nootkatone or isomers of nootkatone such as α-vetivone (isonootkatone).

nootkatol nootkatone

α-vetivone

For isolation and structure of α-vetivone see *Pfau. Plattner, Helv. Chim. Acta.*, 22, 640 (1939): *Naves. Perrottet*, ibid, 24, 3 (1991).

In a fifth aspect the invention provides a pharmaceutical composition comprising a sesquiterpene and one or more pharmaceutically acceptable carrier(s).

In a sixth aspect the invention provides a pharmaceutical composition comprising a sesquiterpene of the invention together with a drug which exhibits instability in the presence of an oxidative enzyme and one or more pharmaceutically acceptable carrier(s). The carriers must be "acceptable" in the sense of being compatible with the sesquiterpene and drug of the invention and not deleterious to the recipients thereof.

This aspect of the invention affords the advantage that the duration of the drug effect can be prolonged enough to reduce the frequency of daily dosage which is likely to improve patient compliance with the treatment regimen.

Preferably, the drug is a dihydropyridine calcium antagonist, especially those which are initially oxidised to their dehydro-derivative by cytochrome P450 3A4. Examples include nifedipine, felodipine, nitrendipene, nisoldipine, amlodipine, isradipine, nicardipine, nilvadipine and nimodipine. For example nitrendipine, a chiral 1,4-dihydropyridine calcium entry blocker, is currently used in the treatment of hypertension. The systemic bioavailability of racemic nitrendipine is low and variable (5% to 30%) despite its almost complete gastrointestinal absorption. This is caused by extensive presystemic biotransformation to the pharmacologically inactive primary pyridine metabolite dehydronitrendipine (M-1) by enzymes of the cytochrome P-450 IIIA family. The inhibitory sesquiterpenes of the invention display a particularly pronounced inhibitory effect in relation to drugs such as nitrendipine which undergo a high degree of first-pass metabolism by cytochrome P450 oxidases.

A particularly preferred drug is cyclosporin. Cyclosporin is a cyclic undecapeptide of fungal origin which forms the cornerstone of therapy for maintenance immunosuppression following transplantation. However, blood concentrations of cyclosporin must be maintained within a relatively narrow range (approximately 100–300 ng ml$^{-1}$) in order to achieve effective immunosuppression with a minimum of nephrotoxicity. This can be a difficult task due, in large part, to the wide inter-patient variability in oral bioavailability ranging from less than 5% to as much as 90%.

Cyclosporin treatments regimes typically cost between 6,800–7,000 US dollars per annum.

Recent studies have suggested, that the poor and variable bioavailability of cyclosporin may relate to pre-systemic metabolism of cyclosporin in the gut wall. The major cyclosporin-metabolizing enzyme appears to be CYP3A4, a cytochrome P-450 enzyme present in high concentrations in the gut wall.

As observed by Ducharme et al, (1993) *Br. J. Clin. Pharmac.*, 36, 457, a compound which inhibits the presystemic metabolism of cyclosporin without systemic effects would be of great clinical value. The compound would improve bioavailability and decrease the cost of therapy through dose reduction in some patients. However, agents known to inhibit CYP3A4 such as erythromycin, verapamil, dilitiazem and ketoconazole have significant adverse effects that make them unsuitable for co-administration with cyclosporin.

Another preferred drug is the antineoplastic agent Taxol® which can be isolated from the bark of the Pacific yew tree, *Taxus brevifolia*. For isolation and structure of Taxol see M. C. Wani et al., *J. Am. Chem. Soc.*, 93, 2325 (1971). For synthesis and anticancer activity of taxol derivatives see D. G. I. Kingston et al, *Studies in Organic Chemistry*, vol 26 entitled "New trends in natural products chemistry 1986", *Atta-ur-Rahman*, P. W. Le Quesne, Eds. (Elsvier, Amsterdam, 1986) pp 219–235.

Taxol® is available commercially from Bristol Myers Squibb.

The preferred oxidised sesquiterpene of the invention, nootkatone, is present in grapefruit juice but not orange juice (which does not have an inhibitory effect on cytochrome P450 enzyme mediated drug metabolism). Hence, the inventors believe that nootkatone is the inhibitory component of grapefruit juice.

As nootkatone is present in natural grapefruit juice it does not appear to be toxic, at least at the concentrations found in normal strength grapefruit juice (approximately 7 mg/200 ml). Thus, the sesquiterpenes of the invention have a clear advantage over known cytochrome P450 enzyme inhibitors which exhibit adverse effects on co-administration with a drug.

Clearly, the unexpected identification of the active inhibitory ingredient in grapefruit juice as a sesquiterpene is of clinical importance, because, due to the variability in the amount of active ingredients between natural grapefruit juice samples, it was impossible previously to quantify an effective inhibitory dose.

The inhibitory sesquiterpenes of the invention can be used with drugs having incomplete first-pass metabolism to produce a more consistent and predictable clinical response. This is particularly useful for drugs with steep concentration-response curves, narrow therapeutic ranges, toxic metabolites or nonlinear pharmacokinetics.

The sesquiterpenes of the invention are especially useful in individuals exhibiting an extensive metaboliser phenotype, identifiable by the genetic test disclosed in UK Patent No. 2,256,271 B.

Preferably, the composition is adapted for oral administration.

Currently, drugs that undergo complete first-pass metabolism are only administered by the intravenous route. The inhibitory sesquiterpenes of the invention permit such drugs to be administered orally, which is more tolerable for patients and better suited to long term treatment.

The compositions of the invention may be in the form of a solid which can be formed for example as tablets, capsules (including spansules) etc. Suitable pharmaceutically acceptable solid carriers include starch, lactose, dextrin and magnesium stearate.

The composition can also be in the form of a liquid, preferably a grapefruit juice flavoured drink. Preferred liquid carriers should be sterile and pyrogen free. Examples are saline and water.

The compositions of the invention can also be adapted for parenteral administration and preferably intravenous administration. Inactivation of drugs in circulating body plasma by oxidative metabolic processes, often associated with the liver, is a well recognised phenomenon. Intravenous co-administration of an inhibitor of cytochrome P450 enzymes offers the potential to reduce this inactivation and so prolong the effective circulating concentration of bioactive compound.

It will be appreciated that the effective ratio of the amount of inhibitory sesquiterpene to the amount of drug will vary depending on the particular drug and its pharmacokinetic characteristics. A skilled worker can readily determine by routine tests an effective ratio of sesquiterpene to drug for use according to the invention. If the drug is cyclosporin for example, the prescribed cyclosporin dose may range from 150 to 350 mg day$^{-1}$. Preferably the amount of sesquiterpene such as the sesquiterpene nootkatone included in the formulation ranges from 7 to 16 mg.

Preferably, the sesquiterpene is present in an amount of from approximately 0.1 to 10 wt % especially 4 to 7 wt % and most preferably 5 wt % based on the amount of the drug in the composition. However, in view of the low toxicity of the sesquiterpenes of the invention it is expected that much higher amounts relative to the amount of drug can be administered without adverse effects.

Treatment with compositions of the invention may consist of a single dose or a plurality of doses over a period of time. The compositions of the invention may be formulated in unit dosage forms, ie. in the form of discrete portions containing a unit dose, or a multiple or sub-unit of a unit dose.

In a sixth aspect the invention provides a product comprising a sesquiterpene and a drug compound which exhibits instability in the presence of an oxidative enzyme as a preparation for simultaneous, separate or sequential use in therapy. Preferably the sesquiterpene is nootkatone, α-vetivone or nootkatol. The drug is preferably cyclosporin, taxol or a dihydropyridine.

In a seventh aspect the invention provides a method of in vitro inhibition of an oxidative enzyme, which method comprises mixing the oxidative enzyme with a substituted or unsubstituted sesquiterpene. Preferably, the sesquiterpene is nootkatone, nootkatol or α-vetivone. Preferably the enzyme is a cytochrome P450 enzyme.

Preferred non-limiting embodiments of the invention will now be described with reference to the accompanying figures in which:

EXAMPLE 1

Measurements of Cytochrome P450 Enzyme Inhibition

Solvents and reagents $^3$H-Cyclosporin A was purchased from Amersham. All other reagents were obtained from BDH (Poole, Dorset, UK) and were of Analar or HPLC grade. Bacto-agar, peptone and yeast extract were purchased from Difco. Glass beads (0.45–0.5 mm) were purchased from Braun Melsungen AG. Thin layer chromatography (TLC) was conducted or Merck (Germany) Silica gel 60 $F_{254}$ size 20×20 cm plastic sheets.

Microorganisms, growth conditions and spectral studies

Human cytochrome P450 3A4 was expressed using the vector pAAH5 (p3A4) in *Saccharomyces cerevisiae* strain AH22 (Guengerich et al., 1991). Plasmid DNA was prepared using Promega's Wizard kit and S. cerevisiae strain AH22 (a his4-519 leu2-3,2-112) was used for transformation. Transformants were grown and maintained at 30° C. on minimal medium containing 2% (w/v) glucose, 0.67% (w/v) Difco yeast nitrogen base without amino acids and 20 µg/ml histidine. Cytochrome P450 content and substrate binding studies were carried out spectrally using a Philips PU8800 US/Vis scanning spectrophotometer according to Omura and Sato (1964) and Jefcoate (1979) respectively. Protein content was determined by the method of Lowry et al. 1956. Yeast microsomal fractions used in reduced carbon monoxide difference spectra, substrate binding studies and metabolism studies were prepared as described previously (Mehmood et al., 1995). This involved mechanical breakage of the yeast cells (harvested at $5 \times 10^7$ cells/ml) using a Braun MSK homogeniser and centrifugation to pellet cells and mitochondria prior to harvesting microsomes after 1 h, 100000 g. Microsomal fractions were resuspended using buffer containing 20% (v/v) glycerol 0.2 M potassium phosphate, 1 mM EDTA pH 7.4 to a final protein concentration of 2 mg/ml. For measurement of cytochrome P450 a few grains of sodium dithionite were added and the sample divided between two cuvettes. CO was bubbled into the sample cuvette and the difference spectrum was recorded between 390–500 nm. Substrate binding spectra were obtained by recording difference spectra between 350 and 500 nm using split-cell cuvettes. The cuvettes contain microsomal fractions or buffer in each chamber of the sample and reference split cuvettes. Nootkatone was added to the microsomal fractions in the sample cuvette but to the buffer in the reference cuvette and difference spectra recorded between 350–500 nm.

In vitro biotransformation

Microsomal samples containing 100 pmoles P450 3A4 and an equivalent concentration of microsomal protein from control yeast containing pAAH5 were preincubated with cyclosporin A (110 pmol; 1 µCi), at 37° C. in buffer containing 20% (v/v) glycerol, 0.2 M potassium phosphate, 1 mM EDTA pH 7.4. The reaction was initiated by the addition of 1 mM NADPH in a final volume of 1 ml and after 30 min. terminated by adding 1 ml ethyl acetate in each reaction mixture. Control experiments confirming the involvement of P450 3A4 in the biotransformation involved the use of microsomes from transformants carrying pAAH5 alone, bubbling carbon monoxide through the reaction for 30 seconds prior to adding substrate and NADPH and lastly the omission of NADPH from reactions. Nootkatone dissolved in DMSO was added at various concentrations to establish inhibitory effects. Microsomal fractions were extracted three times by the addition of 1 ml hexane, vortexing for 20 seconds and separating layers by centrifugation (3000 rev min$^{-1}$) for 3 min. The organic layer was taken and the residual water was removed by adding a few milligrams of anhydrous sodium sulphate. Hexane extracts were dried under a stream of nitrogen at 45° C. in a water bath and resuspended in hexane again for TLC analysis.

Thin layer chromatography

The ethyl acetate extracts from biotransformation studies were directly spotted on to TLC plates and developed in solvent system heptane/pyridine/ethyl acetate (100/75/1 v/v) in a chromatographic tank lined with a blotting paper the same size as the TLC plate. Chromatograms were air-dried and visualised under UV light or in iodine vapours. The Rf valves of spots were measured and compared to the literature. Three metabolites were identified (M1, M6 and M21) and spots corresponding to substrate and metabolic were cut from the chromatogram and eluted twice in 1 ml ethyl acetate. Radioactivity measurements by scintillation counting were used to determine the extent of metabolism.

Guengerich F P, Brian W R, Sari M A, and J T Ross, 1991, Expression of mammalian cytochrome P450 enzymes using yeast-based vectors Methods Enzymol, 206, 130.

Jefcoate C R, 1979, Measurement of substrate and inhibitor binding to microsomal cytochrome P450 by optical difference spectroscopy. Methods Enzymol, 52, 258.

Lowry O H, Rosebrough N J, Farr L and Randali R J, 1951, Protein measurement with the Folin phenol reagent. J. Biol. Chem, 31, 4515.

Mehmood Z, Kelly D E, and S L Kelly, 1995, Metabolism of the herbicide chlortoluron by human cytochrome P450 3A4. Chemosphere, 31, 4515.

Omura T and R J Sato, 1964, The carbon-monoxide pigment of liver microsomes I. Evidence for its haemoprotein nature. J. Biol. Chem. 239, 2370.

Using the above methods the inventors have shown that against cyclosporin as a substrate and monitoring 3 different metabolites produced by human cytochrome P450 3A4, the $IC_{50}$ values (the concentration required to reduce enzymic activity by 50%) are less than 140 µM [micromolar] with nootkatone. Nootkatone has a high affinity for the cytochrome P450 enzyme with a $K_S$ of 80–100 µM.

In similar experiments using nootkatol a less marked inhibitory effect was observed.

EXAMPLE 2

Figure 1:
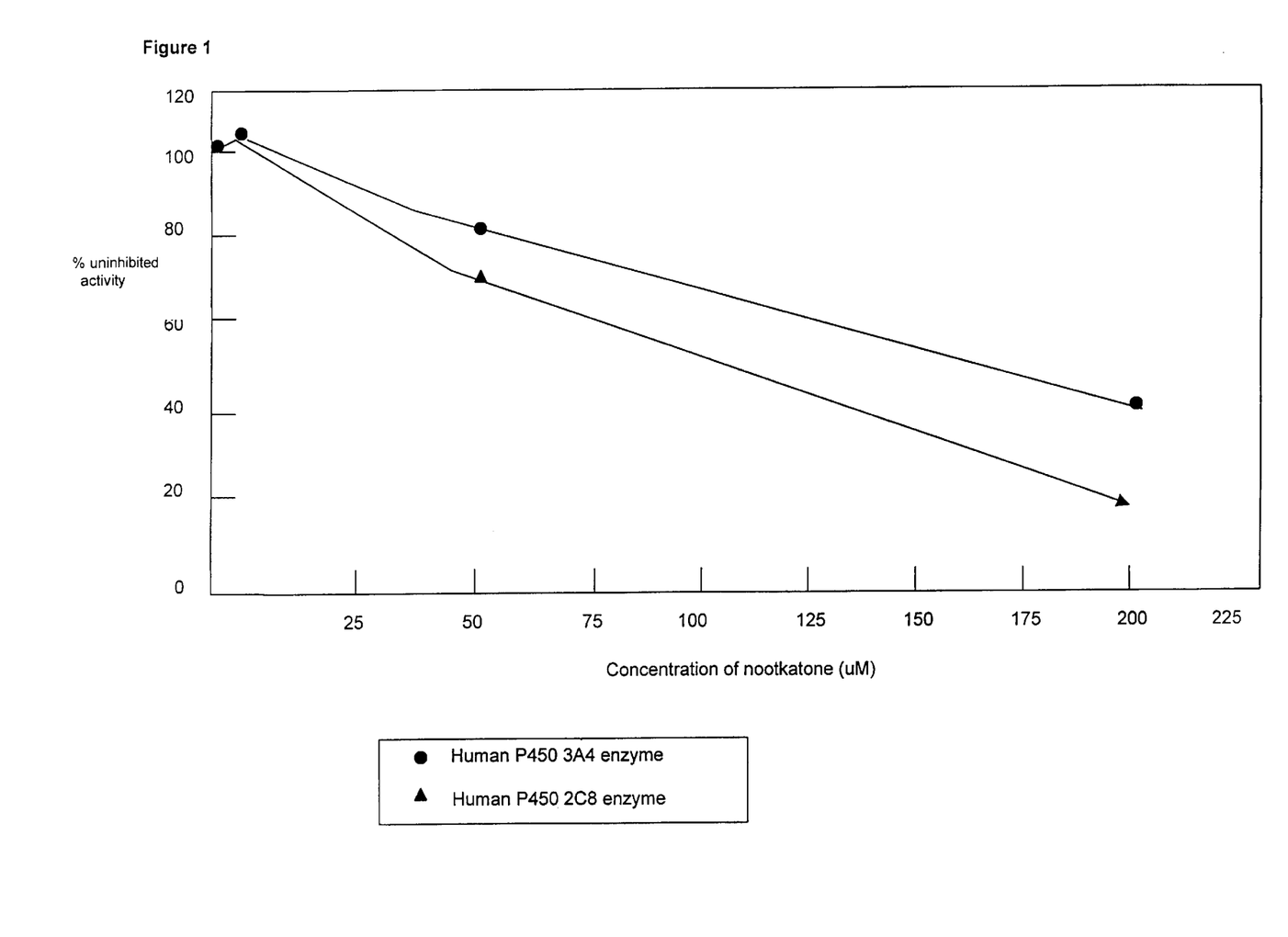
FIG. 1 shows the effect of the oxidised sesquiterpene nootkatone on the formation of metabolites of the anticancer drug Taxol.

Effect of Nootkatone on Taxol Metabolism by Human Cytochrome P450 2C8 and Human Cytochrome P450 3A4 Enzymes The FIG. 1 graph of the effects of nootkatone on the formation of Taxol metabolites gives results of in vitro assays for the inhibition of the conversion of Taxol to 6-hydroxytaxol by human P450 2C8 and the conversion of Taxol to "metabolite B" by human P450 3A4.

It is expected and observed by skilled persons that measurements of in vitro inhibition of these oxidative enzyme systems are indicative of in vivo activities. Thus, for example, literature reference to studies on cytochrome P450 inhibitors (Clin. Pharmacol. Ther., 1991, 50, 394) also quotes supporting references to parallel effects measured for the metabolism of drugs shown in vivo being seen as in vitro.

Use of a sesquiterpene in the inhibition of an oxidative enzyme

The inhibition of an oxidative enzyme can be readily determined by a skilled person in an in vitro test in which the consumption of oxygen by the oxidative enzyme is measured in the presence or absence of a sesquiterpene of the invention. The total inhibition or reduction of oxygen consumption in the presence of a sesquiterpene is indicative of an inhibitory effect of the invention.

EXAMPLE 3

IN VIVO INHIBITION TEST

The in vitro effect of the inhibitory sesquiterpenes of the invention on the metabolism of drugs exhibiting instability in the presence of an oxidative enzyme can be confirmed in vivo using the methods described by Edgar et al, (1992) Eur. J. Clin. Pharmacol., 42: 313–317, the disclosure and supporting references of which are incorporated herein by reference.

Edgar et al (1992) examined the effect of grapefruit juice on the pharmacokinetics in humans of felodipine, but the procedures disclosed can be applied to any drug by a skilled person. Subjects are given a 5 mg dose of the drug and either water (200 ml) or a solution (7 mg in 200 ml water) of the sesquiterpene of the invention. Blood samples (5 ml) are taken for drug and its primary metabolite analysis before and after dosing. Samples are centrifuged and the plasma fraction analysed by gas chromatography. The maximum plasma concentration $C_{max}$ and the time taken to reach the maximum $t_{max}$ are recorded from the individual plasma concentration-time curves. The area under the plasma concentration-time curve from time zero to infinity is calculated.

A positive inhibitory effect on drug metabolism is indicated by an increase in $C_{max}$ and AUC in association with sesquiterpene intake compared to the values obtained with the drug in association with water intake.

EXAMPLE 4

SELECTION METHOD

Detection of Cytochrome P450 Inhibitor Activity in a Whole Cell Assay

The suitability of test sesquiterpene compounds as useful inhibitors of cytochrome P450 enzyme activity can be determined by introducing the test compound to a cell preparation of an organism which produces a relevant oxidative enzyme and to which is added a known substrate for the enzyme system. Thus the hydroxylation of a steroid, such as 4-adrostene-3, 17-dione, by the oxidative enzyme system present in *Bacillus megaterium* ATCC 13368 can be used to detect relevant cytochrome P450 activity. Such cells are available from Schering Corporation, U.S.A. Using the conditions for growth, conversion and detection described in the literature [Dror and Freeman, *Appl. Environ. Microbiol.*, 1995, 61, 855] the test sesquiterpene inhibitor is added to the reaction mixture of grown cells of *Bacillus megaterium* prior to the addition of the steroid substrate and the progress of the hydroxylation assayed chromatographically as described. Test compounds which reduce the extent of hydroxylation of the substrate at levels less than 500 µg/ml are deemed to be suitable inhibitors for use in a method of manufacturing a medicament according to the invention. Preferably, an inhibitor will show activity at 100 µg/ml or less.

EXAMPLE 5

PHARMACEUTICAL FORMULATIONS

The following examples illustrate pharmaceutical formulations according to the invention in which the active ingredient is a drug which exhibits instability in the presence of an oxidative enzyme. The sesquiterpene component is preferably one or more of nootkatone, nootkatol and α-vetivone.

Example A: Tablet

| | |
|---|---|
| Sesquiterpene | 7 mg |
| Active ingredient | 100 mg |
| Lactose | 200 mg |
| Starch | 50 mg |

-continued

| | |
|---|---|
| Polyvinyipyrrolidone | 5 mg |
| Magnesium stearate | 4 mg |
| | 356 mg |

Tablets are prepared from the foregoing ingredients by wet granulation followed by compression.

Example B: Tablet Formulations

The following formulations A and B are prepared by wet granulation of the ingredients with a solution of povidone, followed by addition of magnesium stearate and compression.

| Formulation A | | |
|---|---|---|
| | mg/tablet | mg/tablet |
| (i) Sesquiterpene | 7 | 7 |
| (a) Active ingredient | 250 | 250 |
| (b) Lactose B.P. | 210 | 26 |
| (c) Povidone B.P. | 15 | 9 |
| (d) Sodium Starch Glycolate | 20 | 12 |
| (e) Magnesium Stearate | 5 | 3 |
| | 507 | 507 |

| Formulation B | | |
|---|---|---|
| | mg/tablet | mg/tablet |
| (i) Sesquiterpene | 15 | 15 |
| (a) Active ingredient | 250 | 250 |
| (b) Lactose | 150 | — |
| (c) Avicel PH 101 ® | 60 | 26 |
| (d) Povidone B.P. | 15 | 9 |
| (e) Sodium Starch Glycolate | 20 | 12 |
| (f) Magnesium Stearate | 5 | 3 |
| | 515 | 315 |

| Formulation C | |
|---|---|
| | mg/tablet |
| Sesquiterpene | 7 |
| Active ingredient | 100 |
| Lactose | 200 |
| Starch | 50 |
| Povidone | 5 |
| Magnesium stearate | 4 |
| | 366 |

The following formulations, D and E, are prepared by direct compression of the admixed ingredients. The lactose used in formulation E is of the direction compression type.

| Formulation D | mg/capsule |
|---|---|
| Sesquiterpene | 15 |
| Active Ingredient | 250 |
| Pregelatinised Starch NF15 | 150 |
| | 415 |

| Formulation E | mg/capsule |
|---|---|
| Sesquiterpene | 15 |
| Active Ingredient | 250 |
| Lactose | 150 |
| Avicel ® | 100 |
| | 515 |

Formulation F (Controlled Release Formulation)

The formulation is prepared by wet granulation of the ingredients (below) with a solution of povidone followed by the addition of magnesium stearate and compression.

| | mg/tablet |
|---|---|
| (i) Sesquiterpene | 30 |
| (a) Active Ingredient | 500 |
| (b) Hydroxypropylmethylcellulose Methocel K4M Premium) ® | 112 |
| (c) Lactose B.P. | 53 |
| (d) Povidone B.P.C. | 28 |
| (e) Magnesium Stearate | 7 |
| | 730 |

Drug release takes place over a period of about 6–8 hours and is complete after 12 hours.

Example C: Capsule Formulations

Formulation A

A capsule formulation is prepared by admixing the ingredients of Formulation D in Example B above and filling into a two-part hard gelatin capsule. Formulation B (infra) is prepared in a similar manner.

| Formulation B | mg/capsule |
|---|---|
| (i) Sesquiterpene | 15 |
| (a) Active ingredient | 250 |
| (b) Lactose B.P. | 143 |
| (c) Sodium Starch Glycolate | 25 |
| (d) Magnesium Stearate | 2 |
| | 435 |

| Formulation C | mg/capsule |
|---|---|
| (i) Sesquiterpene | 15 |
| (a) Active ingredient | 250 |
| (b) Macrogol 4000 BP | 350 |
| | 665 |

Capsules are prepared by melting the Macrogol 4000 BP, dispersing the active ingredient and sesquiterpene in the melt and filling the melt into a two-part hard gelatin capsule.

| Formulation D | mg/capsule |
|---|---|
| Sesquiterpene | 15 |
| Active ingredient | 250 |
| Lecithin | 100 |
| Arachis Oil | 100 |
| | 465 |

Capsules are prepared by dispersing the active ingredient in the lecithin and arachis oil and filling the dispersion into soft, elastic gelatin capsules.

Formulation E (Controlled Release Capsule)

The following controlled release capsule formulation is prepared by extruding ingredients i, a, b, and c using an extruder, followed by spheronisation of the extrudate and drying. The dried pellets are then coated with release-controlling membrane (d) and filled into a two-piece, hard gelatin capsule.

| | mg/capsule |
|---|---|
| (i) Sesquiterpene | 15 |
| (a) Active ingredient | 250 |
| (b) Microcrystalline Cellulose | 125 |
| (c) Lactose BP | 125 |
| (d) Ethyl Cellulose | 13 |
| | 528 |

Example D: Injectable Formulation

| | |
|---|---|
| Sesquiterpene | 0.01 g |
| Active ingredient | 0.200 g |
| Sterile, pyrogen free phosphate buffer (pH 7.0) to | 10 ml |

The active ingredient and terpene are dissolved in most of the phosphate buffer (35–40° C.), then made up to volume and introduced into a sterile 10 ml amber glass vial (type 1) and sealed with sterile closures and overseals.

Example E: Intramuscular injection

| | |
|---|---|
| Sesquiterpene | 0.10 g |
| Active ingredient | 0.20 g |
| Benzyl Alcohol | 0.10 g |

-continued

|  |  |
|---|---|
| Glucofurol 75 ® | 1.45 g |
| Water for Injection q.s. to | 3.00 ml |

The active ingredient and sesquiterpene are dissolved in the glycofurol. The benzyl alcohol is then added and dissolved, and water added to 3 ml. The mixture is then filtered through a sterile micropore filter and sealed in sterile 3 ml glass vials (type 1).

Example F: Syrup Suspension

|  |  |
|---|---|
| Sesquiterpene | 0.0125 g |
| Active ingredient | 0.2500 g |
| Sorbitol Solution | 1.5000 g |
| Glycerol | 2.0000 g |
| Dispersible Cellulose | 0.0750 g |
| Sodium Benzoate | 0.0050 g |
| Flavour, Peach 17.42.3169 | 0.0125 ml |
| Purified Water q.s. to | 5.0000 ml |

The sodium benzoate is dissolved in a portion of the purified water and the sorbitol solution added. The terpene and active ingredient are added and dispersed. In the glycerol is dispersed the thickener (dispersible cellulose). The two dispersions are mixed and made up to the required volume with the purified water. Further thickening is achieved as required by extra shearing of the suspension.

Example G: Suppository

|  | mg/suppository |
|---|---|
| Sesquiterpene (63 µm)* | 15 |
| Active ingredient (63 µm)* | 250 |
| Hard Fat, BP (Witepsol H15 - Dynamit Nobel) | 1770 |
|  | 2035 |

*The sesquiterpene and active ingredient are used as a powder wherein at least 90% of the particles are of 63 µm diameter or less.

One fifth of the Witepsol H15 is melted in a steam-jacketed pan at 45° C. maximum. The sesquiterpene and active ingredient are sifted through a 200 µm sieve and added to the molten base with mixing, using a silverson fitted with a cutting head, until a smooth dispersion is achieved. Maintaining the mixture at 45° C., the remaining Witepsol H15 is added to the suspension and stirred to ensure a homogenous mix. The entire suspension is passed through a 250 µm stainless steel screen and, with continuous stirring, is allowed to cool to 40° C. At a temperature of 38° C. to 40° C. 2.02 g of the mixture is filled into suitable plastic moulds. The suppositories are allowed to cool to room temperature.

Example H: Pessaries

|  | mg/pessary |
|---|---|
| Sesquiterpene | 15 |
| Active ingredient | 250 |
| Anhydrate Dextrose | 380 |

-continued

|  | mg/pessary |
|---|---|
| Potato Starch | 363 |
| Magnesium Stearate | 7 |
|  | 1015 |

The above ingredients are mixed directly and pessaries prepared by direct compression of the resulting mixture.

What is claimed is:

1. A composition comprising:
   i) a pharmaceutically acceptable carrier;
   ii) a compound which is unstable in the presence of an oxidative enzyme; and
   iii) a sesquiterpene, wherein said sesquiterpene is selected from the group consisting of nootkatol, nootkatone, nootkatol isomers, and nootkatone isomers.

2. The composition of claim 1, wherein said compound is selected from the group consisting of taxol, cyclosporin, and dihydropyridine.

3. The composition of claim 1, wherein said sesquiterpene comprises approximately 0.1 to 10% of said composition.

4. The composition of claim 1, wherein said composition is a solid.

5. The composition of claim 1, wherein said composition is a liquid.

6. The composition of claim 1, wherein said composition is suitable for administration to humans, wherein said administration is selected from the group consisting of oral administration and intravenous administration.

7. The composition of claim 1, wherein said oxidative enzyme is a cytochrome P450 enzyme.

8. The composition of claim 7, wherein said cytochrome P450 enzyme is cytochrome P450 3A4.

9. A method for inhibiting the action of at least one oxidative enzyme, comprising the steps of:
   a) providing in any order:
      i) a composition comprising a pharmaceutically acceptable carrier, a compound which is unstable in the presence of an oxidative enzyme, and a sesquiterpene, wherein said sesquiterpene is selected from the group consisting of nootkatol, nootkatone, nootkatol isomers, and nootkatone isomers; and
      ii) one or more oxidative enzymes; and
   b) exposing said composition to said one or more oxidative enzymes under conditions such that said one or more oxidative enzymes is inhibited.

10. The method of claim 9, wherein said compound is selected from the group consisting of taxol, cyclosporin, and dihydropyridine.

11. The method of claim 9, wherein said sesquiterpene comprises approximately 0.1 to 10% of said composition.

12. The method of claim 9, wherein said composition is a solid.

13. The method of claim 9, wherein said composition is a liquid.

14. The method of claim 9, wherein said composition is suitable for administration to humans, wherein said administration is selected from the group consisting of oral administration and intravenous administration.

15. The method of claim 9, wherein said oxidative enzyme is a cytochrome P450 enzyme.

16. The method of claim 15, wherein said cytochrome P450 enzyme is cytochrome P450 3A4.

17. The method of claim 9, wherein said inhibition is in vitro.

18. A method for inhibiting the action of at least one oxidative enzyme, comprising the steps of:
a) providing in any order:
i) a composition comprising a pharmaceutically acceptable carrier, a sesquiterpene, and a compound which is unstable in the presence of an oxidative enzyme, wherein said compound is selected from the group consisting of taxol and cyclosporin; and
ii) one or more oxidative enzymes; and
b) exposing said composition to said one or more oxidative enzymes under conditions such that said one or more oxidative enzymes is inhibited.

19. The method of claim 18, wherein said sesquiterpene is selected from the group consisting of nootkatol, nootkatone, nootkatol isomers, nootkatone isomers, bicyclic sesquiterpenes, substituted sesquiterpenes, and oxidized sesquiterpenes.

20. The method of claim 18, wherein said sesquiterpene comprises approximately 0.1 to 10% of said composition.

21. The method of claim 18, wherein said composition is a solid.

22. The method of claim 18, wherein said composition is a liquid.

23. The method of claim 18, wherein said composition is suitable for administration to humans, wherein said administration is selected from the group consisting of oral administration and intravenous administration.

24. The method of claim 18, wherein said oxidative enzyme is a cytochrome P450 enzyme.

25. The method of claim 24, wherein said cytochrome P450 enzyme is cytochrome P450 3A4.

26. The method of claim 18, wherein said inhibition is in vitro.

27. A method for preparing a pharmaceutical composition comprising the steps of:
a) providing in any order:
i) a sesquiterpene selected from the group consisting of nootkatol, nootkatone, nootkatol isomers, and nootkatone isomers;
ii) a pharmaceutically acceptable carrier; and
iii) a compound which is unstable in the presence of an oxidative enzyme; and
b) combining said sesquiterpene, said pharmaceutically acceptable carrier, and said compound which is unstable in the presence of said oxidative enzyme under conditions such that a pharmaceutical composition is produced.

28. The method of claim 27, wherein said compound is selected from the group consisting of taxol, cyclosporin, and dihydropyridine.

29. The method of claim 27, wherein said sesquiterpene comprises approximately 0.1 to 10% of said pharmaceutical composition.

30. The method of claim 27, wherein said pharmaceutical composition is a solid.

31. The method of claim 27, wherein said pharmaceutical composition is a liquid.

32. The method of claim 27, further comprising the step of:
c) administering said pharmaceutical composition to a human, wherein said administration is selected from the group consisting of oral administration and intravenous administration.

33. The method of claim 27, wherein said oxidative enzyme is a cytochrome P450 enzyme.

34. The method of claim 33, wherein said cytochrome enzyme is cytochrome P450 3A4.

35. The method of claim 27, wherein said pharmaceutical composition is stable in vivo.

36. The method of claim 27, wherein said pharmaceutical composition is stable in vitro.

* * * * *

UNITED STATES PATENT AND TRADEMARK OFFICE
CERTIFICATE OF CORRECTION

PATENT NO. : 6,054,490
DATED : 04/25/00
INVENTOR(S) : John Thomas SIME et al.

It is certified that error appears in the above-identified patent and that said Letters Patent is hereby corrected as shown below:

In column 1, line 5, please delete "May 4, 1996" and insert --May 9, 1996--.

Signed and Sealed this

Twenty-seventh Day of February, 2001

Attest:

NICHOLAS P. GODICI

Attesting Officer

Acting Director of the United States Patent and Trademark Office